(12) United States Patent
Lecouvey et al.

(10) Patent No.: US 7,005,533 B2
(45) Date of Patent: Feb. 28, 2006

(54) BISPHOSPHONATE DERIVATIVES, THEIR PREPARATIONS AND USES

(75) Inventors: Marc Lecouvey, Paris (FR); Yves Leroux, Paris (FR); Michel Kraemer, Paris (FR); Michel Crepin, Paris (FR); Driss El Manouni, Paris (FR); Malika Louriki, Noisy le Sec (FR)

(73) Assignee: Universite Paris 13, Villetaneuse (FR)

( * ) Notice: Subject to any disclaimer, the term of this patent is extended or adjusted under 35 U.S.C. 154(b) by 0 days.

(21) Appl. No.: 10/887,895

(22) Filed: Jul. 12, 2004

(65) Prior Publication Data

US 2004/0266735 A1    Dec. 30, 2004

Related U.S. Application Data

(62) Division of application No. 10/194,058, filed on Jul. 15, 2002, now abandoned.

(60) Provisional application No. 60/365,819, filed on Mar. 21, 2002, provisional application No. 60/307,598, filed on Jul. 26, 2001.

(30) Foreign Application Priority Data

Jul. 16, 2001   (FR) .................................. 01 09483

(51) Int. Cl.
*C07F 9/02* (2006.01)
*C07F 9/38* (2006.01)
(52) U.S. Cl. ........................... 558/161; 562/11; 562/13
(58) Field of Classification Search .................. 562/11, 562/13; 558/161
See application file for complete search history.

(56) References Cited

U.S. PATENT DOCUMENTS 6,534,488 B1 * 3/2003 Gibson et al. .............. 514/102

* cited by examiner

*Primary Examiner*—Johann Richter
*Assistant Examiner*—Ebenezer Sackey
(74) *Attorney, Agent, or Firm*—Buchanan Ingersoll PC

(57) ABSTRACT

The present invention relates to derivatives of 1-hydroxymethylene-1,1-bisphosphonic acid, the pharmaceutical compositions comprising them, and their application in therapeutics, particularly for the treatment of cancerous tumors. It is also directed to a methods of preparation of such derivatives.

8 Claims, 4 Drawing Sheets

BISPHOSPHONATE DERIVATIVES, THEIR PREPARATIONS AND USES

Figure 1:
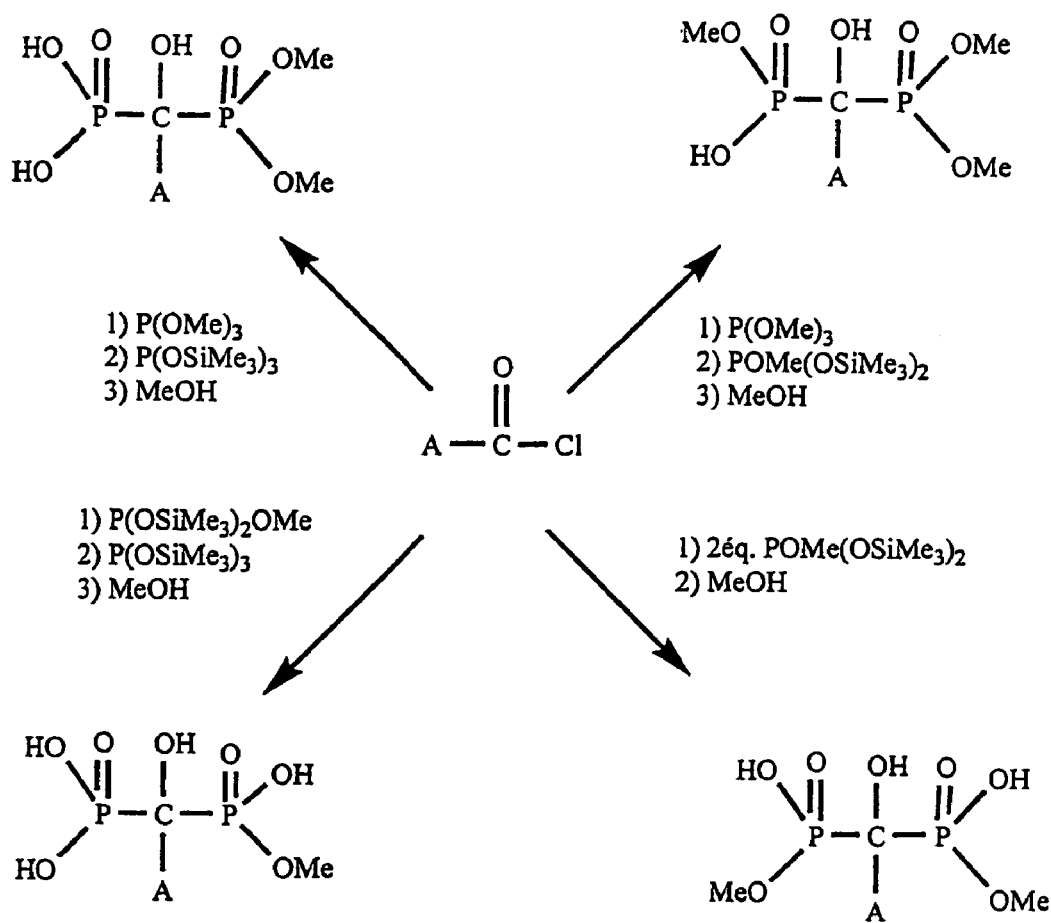

This present application is a Divisional Application of U.S. Ser. No. 10/194,058, entitled "New Bisphosphonate Derivatives, their Preparation and Uses," filed Jul. 15, 2002 now abandoned, which claims priority under 35 U.S.C. § 119 to French Application No. 01 09483, filed on Jul. 16, 2001, U.S. Provisional Application No. 60/307,598, entitled "New Bisphonic Acid Derivative, a Process for the Preparation thereof, and the Use thereof in Therapy," filed on Jul. 26, 2001, and U.S. Provisional Application No. 60/365,819, entitled "Nouveaux Derives de Bisphosphonates, Leurs Preparations et Utilsations," filed on Mar. 21, 2002, the contents of which are hereby incorporated by reference in their entirety.

FIELD OF THE INVENTION

The present invention relates to new derivatives of 1-hydroxymethylene-1,1-bisphosphonic acid or bisphosphonate, the pharmaceutical compositions comprising them, and their application in therapeutics, particularly for the treatment of cancerous tumors and viral or inflammatory hepatic diseases. It also discloses methods of preparation of such derivatives.

BACKGROUND OF THE INVENTION

Derivatives of 1-hydroxymethylene-1,1-bisphosphonic acid display remarkable antitumoral properties and their medical applications have been therefore the subject of in-depth research. Such derivatives, characterized by a P—C—P bond, are stable analogs of pyrophosphate and are resistant to enzymatic hydrolysis. Regarding the therapeutic applications of diphosphonic acid derivatives, it is well known that various derivatives have properties useful in the treatment of inflammation, osteoporosis or some bone metastasis. In particular, they are used for their ability to inhibit bone resorption to treat numerous diseases characterized by abnormal calcium metabolism. Bone resorption is pathologically increased in metastasis of certain types of cancer such as breast or prostate cancer, and is accelerated in different forms of osteoporosis including that related to age. Patients with this type of metastasis can now benefit from treatment regimens including bisphosphonates (Diel et al., 2000; Lipton, 2000; Mincey et al., 2000). It should be pointed out that bone is the third most common site of metastasis and that over 80% of patients who die from cancer have bone tumors at autopsy.

A number of diphosphonic acid derivatives and their properties useful in various applications have been described in the literature.

For example, didronic acid has been known for years as active for drugs in the treatment of bone diseases such as osteoporosis, and more particularly disodium didronate described in French patent 8,441 M. A derivative is described for example in U.S. Pat. No. 4,705,561 relating to alendronic acid which inhibits bone resorption and which can be used in the treatment of osteoporosis. Another similar structure is described in British patent 2,312,165 relating to ibandronic acid having anti-inflammatory properties.

Alkane-1,1-diphosphonic acid with an amino-acid, and possessing antitumor and bone resorption activities have been described in PCT patent application WO 97/49711. Other diphosphonic acid derivatives comprising a phenyl substituent at the 1 position are described in U.S. Pat. No. 4,473,560 which discloses their anti-inflammatory activity, more particularly a antiarthritic activity, or in PCT patent application WO 97/04785 relating to phenol substituted diphosphonates having antineoplasic activity. Further, European patent EP 537,008 describes diphosphonate derivatives having a lipophilic group, which are useful in the preparation of a medicament inhibiting protein prenyl transferase, likely to block the neoplasic transformation resulting from ras oncogenes.

This anti-osteoclastic action of bisphosphonates is postulated to occur by induction of apoptosis in osteoclasts (Luckman et al., 1998) via inhibition of the mevalonate pathway and of cholesterol synthesis.

Bisphosphonates inhibit in vitro the proliferation of breast tumor cells (Fromigue et al., 2000; Hiraga et al., 2001; Jagdev et al., 2001; Senaratne et al., 2000; Yoneda et al., 2000) and prostate tumor cells (Lee et al., 2001). This in vitro inhibition is due to apoptosis of tumor cells and is accompanied by expression of the bcl-2 gene (Senaratne et al., 2000) and activation of caspases (Fromigue et al., 2000).

Besides the hereinabove effects, bisphosphonates may have several additional actions, such as inhibition in vitro of adhesion of breast tumor cells to bone matrices (Boissier et al., 1997; Van der Pluijm et al., 1996), induction in vitro of myeloma cell apoptosis (Shipman et al., 1997, 1998, 2000a) or inhibition of the activity (but not the production) of matrix metalloproteinases in breast or prostate carcinoma cells (Boissier et al., 2000; Ichinose et al., 2000; Teronen et al., 1997).

Bisphosphonates have also been utilized in the treatment of lymphoblastic leukemia (Ogihara et al., 1995; Takagi et al., 1998). Leukemic cells induce angiogenesis in bone marrow, this being necessary for their proliferation. Treatment of lymphoblastic leukemia with bisphosphonates is accompanied by a significant decrease in angiogenesis (Perez-Atayde et al., 1997).

Recent data point toward the very likely involvement of angiogenic factors in the formation of bone metastases. For instance, in a study in an in vivo murine model of experimental breast tumor cell metastasis (MDA MB 231), Van der Pluijm et al. (2001) hypothesized that elevated expression of angiogenic (VEGF) and osteolytic (PTH) factors in the tumor cells is involved in osteotropism and bone loss of bone metastases.

Although the antiproliferative activity of bisphosphonates on tumor cells in vitro is now well established, the question of whether bisphosphonates can exert antitumoral action in vivo is still open. Some data appear to argue for an antiproliferative action of bisphosphonates in vivo, at metastatic sites in bone. For instance, according to Hiraga et al. (2001), bisphosphonates would diminish the tumor burden of metastatic cells in bone. However, to our knowledge, no data have been reported on an antitumoral action of bisphosphonates in vivo on primary tumors.

Bisphosphonates are metabolized by the body to a low extent and the active fraction represents only 3 to 7% of the absorbed dose. This low bioavailability of bisphosphonates after oral administration results from their low lipophilicity (Lin, 1996) which is due to their high state of ionization at physiologic pH. Their absorption is further reduced by the strong negative charge and fairly large size of these molecules (Ruifrok and Mol, 1983; Pade and Stavchanvsky, 1997). Moreover, the absorption of bisphosphonates is reduced further still by their high level of complexation with calcium and other divalent ions in the intestine (Lin, 1996).

Their administration often causes gastrointestinal symptoms and other side effects (Adami and Zamberlan., 1996; Mondelo et al., 1997).

Moreover, drug acquired resistance is now a major concern in the cancer therapy, and most of human cancers are resistant to the effects of chemiotherapies.

To improve their therapeutic effects, various approaches have been proposed. The first consists in the use of a peptide vector grafted to the side chain of hydroxybisphosphonic acid (Ezra et al., 2000). Other studies suggest encapsulating the drug in microspheres (Patashnik et al., 1997) or in liposomes (Ylitalo et al., 1998).

The present invention is therefore directed at providing new bisphosphonate derivatives with improved bioavailability and satisfactory therapeutic efficacy.

Two methods of synthesis described in the literature yield 1-hydroxymethylene-1,1-bisphosphonic acids.

In the first, the desired products are obtained in a single step. This method consists in heating a mixture of carboxylic acid in the presence of phosphorous acid and phosphorus trichloride at 100° C. for several hours.

The conditions of this reaction have been studied in great detail. In fact, since 1970, more than fifty patents and articles have been published. The drawbacks of this method, however, are numerous. Indeed, the drastic operating conditions are not suited to labile substrates. Furthermore, extraction of the bisphosphonate from the reaction medium is often tricky.

The second procedure is an indirect method involving synthesis of 1-hydroxymethylene-1,1-bisphosphonic esters followed by a dealkylation step. The α-ketophosphonates are typically prepared via a Michaelis Arbuzov reaction, starting from a phosphite with the structure $P(OR)_3$ and an acid chloride. The bisphosphonic ester is then normally obtained by reaction of the α-ketophosphonate with a dialkylphosphite $HOP(OR)_2$.

The dealkylation step is carried out either by hydrolysis in hydrochloric acid or by treatment with bromotrimethylsilane followed by methanolysis.

Unfortunately, neither of these two synthetic methods yields partially esterified 1-hydroxymethylene-1,1-bisphosphonic acids.

The present invention therefore equally proposes methods of preparation of bisphosphonates allowing regioselective addition of one or more ester functions on the phosphonic acid moieties.

SUMMARY OF THE INVENTION

Therefore, one object of the present invention comprises the bisphosphonate derivatives represented by the following formula (I) or (I'):

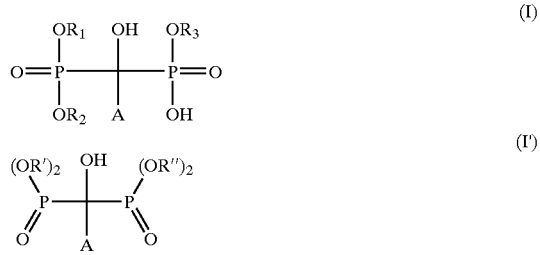

wherein $R_1$, $R_2$ and $R_3$, which are the same or different, each represent a hydrogen atom, an alkyl, aryl, acyloxyalkyl or heterocycle group, and R' and R", which are the same or different, each represent a hydrogen atom, an alkali metal or alkaline earth atom, A represents a group with the formula $—(CH_2)n-R_4$, $R_4$ represents a hydrogen atom, an alkyl group, an aryl group, a heterocycle or a group with the formula $—NR_5R_6$, $R_5$ and $R_6$, which are the same or different, represent a hydrogen atom or an alkyl group, n is a whole number from 0 to 24 inclusive, with the exception of compounds represented by formula (I) in which $R_1$, $R_2$ and $R_3$ simultaneously represent a hydrogen atom, and compounds represented by formula (I') in which R' and R" simultaneously represent a hydrogen atom, their optical and geometrical isomers, their racemates, their salts, their hydrates and their mixtures.

The present invention provides therefore compounds which present advantageously a good bioavailability, in particular when compared to compounds already used or described as therapeutic agents, such as for instance Etidronate (Procter & Gamble), Alendronate (Merck), Pamidronate (Novartis), Olpadronate (Gador), Ibandronate (Borhinger-Mannheim), compound EB1053 (Leo), compound YH 529 (Aventis) or Residronate (Procter & Gamble).

Another object of the present invention is a pharmaceutical composition comprising at least one compound represented by formula (I) or (I') such as described hereinabove, possibly in association with another therapeutically active substance, in a pharmaceutically acceptable support.

It further relates to a method of treating a disorder characterized by abnormal calcium metabolism, such as cancers or osteoporosis, comprising administering to a patient in need of such treatment a therapeutically effective amount of at least one compound represented by formula (I) or (I').

Another object of the present invention is a method for treating viral or inflammatory hepatic disease, comprising administering to a patient in need of such treatment a therapeutically effective amount of at least one compound represented by formula (I) or (I').

A final object of the present invention is methods for producing compounds represented by formula (I) or (I').

LEGEND TO THE FIGURES

FIG. 1: Reaction diagrams of the method of preparation of compounds according to the invention. A is defined as hereinabove.

Figure 2:
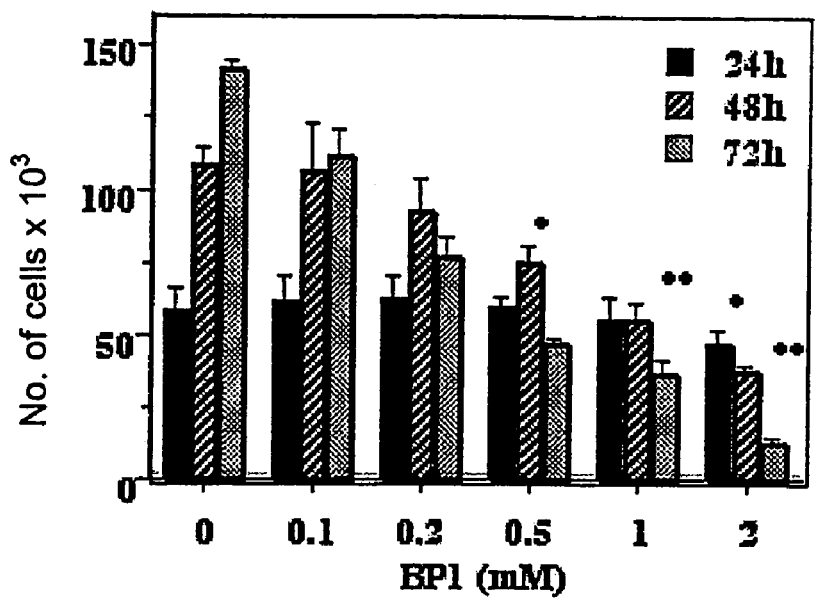
Figure 3:
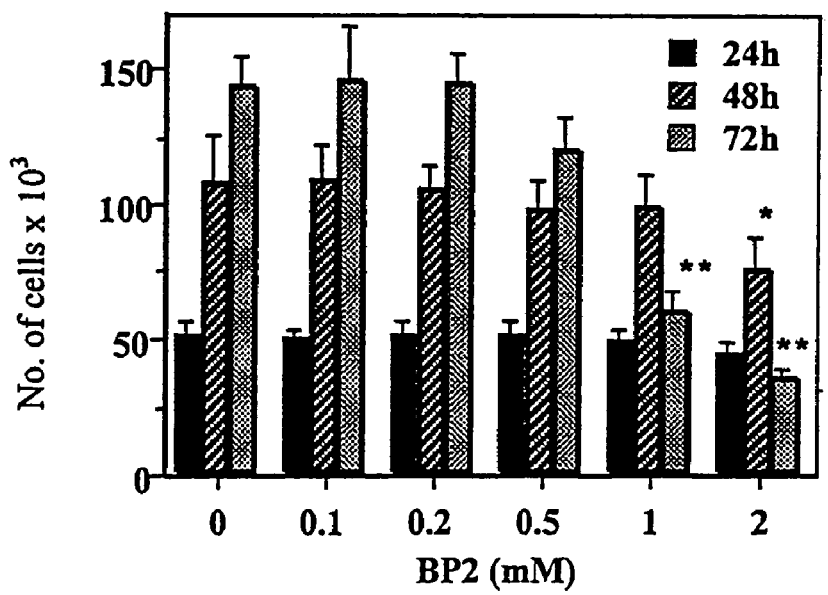

FIGS. 2 and 3: Inhibition in vitro of the proliferation of A 431 tumor cells by BP1 (FIG. 2) and BP2 (FIG. 3) respectively, after 24, 48 and 72 h of culture. Results are expressed as number of cells±SE (bars). *P<0.05; **P<0.01 compared to controls.

Figure 4:
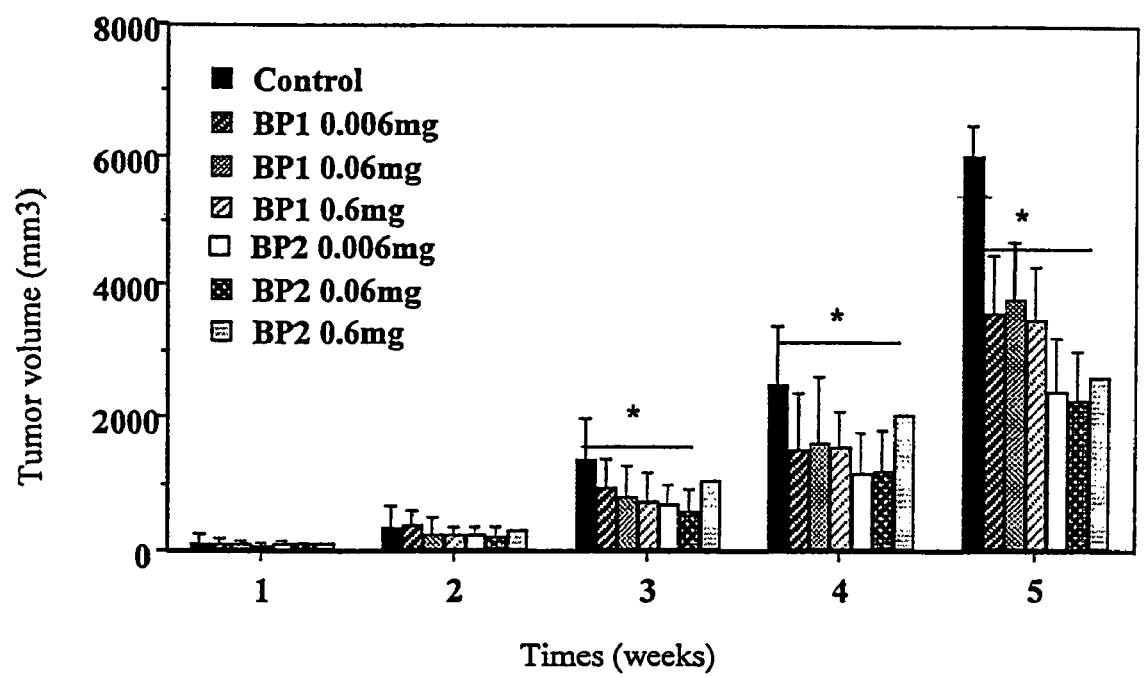

FIG. 4: Inhibition in vivo of the growth of A 431 tumors by BP1 and BP2. Implantation of A431 cells in nude mice induces formation of subcutaneous tumors. One week after injection of the cells, the tumors were treated with BP1 and BP2 at doses of 0.006, 0.06 and 0.6 mg/mouse, twice a week for 5 weeks. Results are expressed as tumor volume±SE (bars). *P<0.05 compared to controls.

Figure 5:
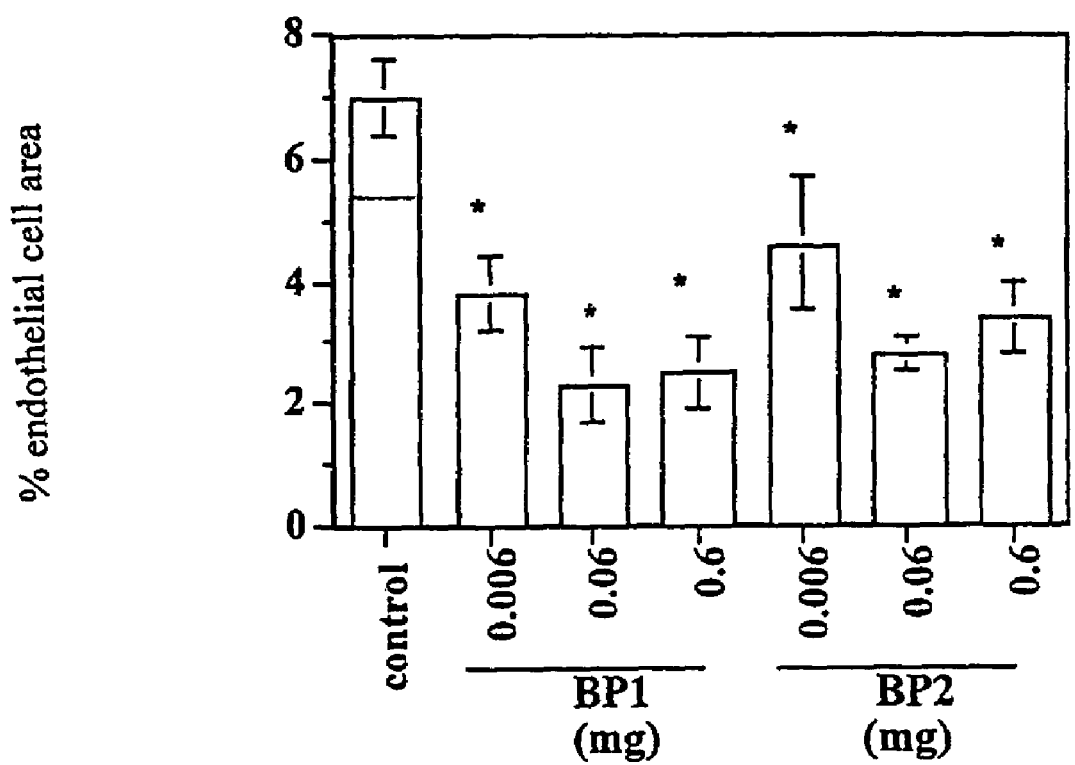

FIG. 5: Immunohistochemical analysis of angiogenesis of A 431 tumors. Endothelial cells were detected with a specific marker (GSL 1). Results are expressed as area±SE (bars) of endothelial cells quantified by image analysis (NIH image). *P<0.01 compared to controls.

DETAILED DESCRIPTION OF THE INVENTION

Therefore, one object of the present invention comprises the bisphosphonate derivatives represented by the following formula (I) or (I'):

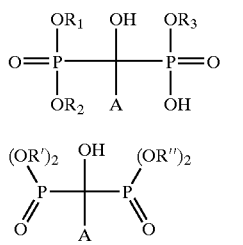

wherein $R_1$, $R_2$ and $R_3$, which are the same or different, each represent a hydrogen atom, an alkyl, aryl, acyloxyalkyl or heterocycle group, and R' and R", which are the same or different, each represent a hydrogen atom, an alkali metal or alkaline earth atom, A represents a group with the formula —$(CH_2)n$-$R_4$, $R_4$ represents a hydrogen atom, an alkyl group, an aryl group, a heterocycle or a group with the formula —$NR_5R_6$, $R_5$ and $R_6$, which are the same or different, represent a hydrogen atom or an alkyl group, n is a whole number from 0 to 24 inclusive, with the exception of compounds represented by formula (I) in which $R_1$, $R_2$ and $R_3$ simultaneously represent a hydrogen atom, and compounds represented by formula (I') in which R' and R" simultaneously represent a hydrogen atom, their optical and geometrical isomers, their racemates, their salts, their hydrates and their mixtures.

The alkyl, aryl, heterocycle or acyloxyalkyl groups described hereinabove are possibly substituted by at least one group chosen from among an aryl group, a heterocycle group, a heterocycloalkyl group, an alkyl group, an alkenyl group, an alkynyl group, an alkylthio group, a halogen atom, preferably Cl, F, Br, a hydroxyl group, an $NO_2$ group, an alkoxy group, an ester group (—COOR), an amino group —NRR''', an acid moiety, an amide group (—CONHR or —NHCOR), wherein R and R''' represent, independently of each other, a hydrogen atom, an alkyl, aryl, heteroaryl or acyloxyalkyl group.

In the context of the present invention, the term "alkyl" more specifically means a linear, branched or cyclic hydrocarbon group having 1 to 24, preferably 1 to 12, carbon atoms such as methyl, ethyl, propyl, isopropyl, butyl, isobutyl, tert-butyl, pentyl, neopentyl, n-hexyl. $C_1$–$C_6$ groups are especially preferred. Methyl and ethyl groups are more especially preferred. The alkyl group may possibly be interrupted by one or more heteroatoms, preferably N, S, O or P.

The term <<alkenyl>> refers to a hydrocarbon group having at least one unsaturated ethylene bond and the term <<alkynyl>> refers to a hydrocarbon group having at least one unsaturated acetylene bond.

The <<aryl>> groups are mono-, bi- or tri-cyclic aromatic hydrocarbons having from 6 to 18 carbon atoms. Examples include a phenyl, α-naphthyl, β-naphthyl or anthracenyl group, in particular.

<<Alkoxy>> groups correspond to the alkyl groups defined hereinabove bonded to the rest of the compound by an —O— (ether) bond.

<<Alkylthio>> groups correspond to the alkyl groups defined hereinabove bonded to the rest of the compound by an —S— (thioether) bond.

<<Acyloxyalkyl>> groups are acyloxy groups bonded to the rest of the compound by an alkyl chain (C1–24), preferably C1–4. Acyloxymethyl and pivaloyloxymethyl groups are specific examples.

<<Halogen>> is understood to mean a fluorine, chlorine, bromine or iodine atom.

<<Heteroatom>> is understood to mean an atom chosen from among O, N and S.

Arylalkyl (or aralkyl) groups are groups comprising an aryl function as defined hereinabove bonded to the rest of the compound by means of an alkyl chain.

<<Heterocycle>> or <<heterocycloalkyl>> groups are groups containing 5 to 18 rings comprising one or more heteroatoms (generally N, O, S or P), preferably 1 to 5 endocyclic heteroatoms. They may be mono-, bi- or tricyclic. They may be aromatic or not. Preferably, and more specifically for $R_5$, they are aromatic heterocycles. Examples of aromatic heterocycles include pyridine, pyridazine, pyrimidine, pyrazine, furan, thiophene, pyrrole, oxazole, thiazole, isothiazole, imidazole, pyrazole, oxadiazole, triazole, thiadiazole and triazine groups. Examples of bicycles include in particular quinoline, isoquinoline and quinazoline groups (for two 6-membered rings) and indole, benzimidazole, benzoxazole, benzothiazole and indazole (for a 6-membered ring and a 5-membered ring). Nonaromatic heterocycles comprise in particular piperazine, piperidine, etc.

The alkaline metal atoms include sodium and potassium. The alkaline earth atoms include calcium.

In formula (I') as defined above, R' and/or R" represent preferably an hydrogen atom or sodium, calcium or potassium atom.

The preferred compounds are represented by formula (I) wherein $R_1$, $R_2$ and $R_3$ are a hydrogen atom or an alkyl group of C1–12, more particularly C1–6.

Advantageously, at least two of the substituents $R_1$, $R_2$ and $R_3$ are different from a hydrogen atom.

In an especially preferred variant of the invention, the substituents $R_1$, $R_2$ and $R_3$, which are different from a hydrogen atom, are identical.

The preferred compounds are represented by formula (I) wherein $R_1$, $R_2$ and $R_3$ represent a methyl or ethyl group.

The preferred compounds are represented by formula (I) or (I') in which A represents a group with formula —(CH2)n-$R_4$, wherein n is a whole number from 1 to 12 inclusive, preferably from 1 to 6 inclusive, advantageously from 1 to 3 inclusive.

The preferred compounds are represented by formula (I) or (I') in which $R_4$ is a C1–C6 alkyl group, a heterocycle, a phenyl group, or a group with formula —$NR_5R_6$, in which $R_5$ and $R_6$, which are the same or different, represent a hydrogen atom or an alkyl group of C1 to C6, wherein n is advantageously a whole number from 1 to 6 inclusive, preferably from 1 to 3 inclusive.

According to a particular embodiment of the invention, the preferred compounds have the formula (I) or (I') wherein A is a group chosen from:

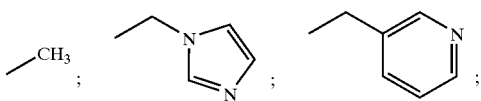

-continued

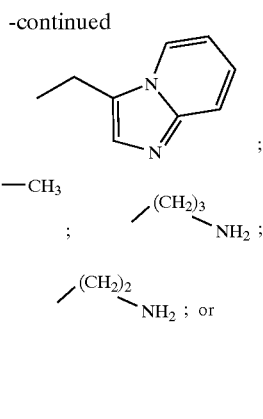

In a particular embodiment, compounds of formula (I') are compounds wherein A represents

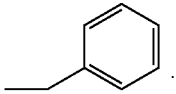

The compounds according to the invention, and in particular compounds of formula (I), have the advantage of improved bioavailability and therefore a highly satisfactory therapeutic effect. In fact, without ascribing to any particular theory of the invention, the ester bonds of the compounds according to the invention increase the lipophilicity of the latter and in this manner in particular the compounds appear to more efficiently cross the gastrointestinal barrier when administered orally, the ester bonds then being lysed to release the corresponding bisphosphonic acid.

The subject of the present invention relates also to methods of preparation of compounds represented by formula (I) and (I').

These methods of preparation have many advantages. They are simple to implement on an industrial scale and produce high yields of bisphosphonates.

The method for preparing compounds of formula (I) disclosed in the present invention comprises the following steps:

contacting (or reacting) at least one acid halide represented by formula (II): ACOX, or one α-ketophosphonate represented by formula (III):

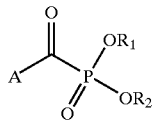

with at least one silyl phosphite represented by formula (IV):

$$P[(OSialk_3)_x][OR_3]_{3-x} \qquad (IV)$$

wherein $R_1$, $R_2$ and $R_3$, which are the same or different, represent an alkyl, aryl, acyloxyalkyl or heterocycle group, A being defined hereinabove, X represents a halogen atom, preferably chlorine, alk is a C1–6 alkyl group, x is 2 or 3, hydrolysis of the compounds obtained in the previous step.

The C1–6 alkyl group is such as defined hereinabove.

The halogen atom may be a chlorine, bromine, iodine or fluorine atom, preferably X is a chlorine atom.

When $R_1$ and $R_2$ are different from a hydrogen atom, the method of preparation of compounds represented by formula (I) advantageously comprises the following steps:

contacting at least one acid halide represented by formula (II): ACOX with at least one phosphite represented by formula (V): P(OR1)(OR2)(OR), wherein $R_1$, $R_2$ and R, which are the same or different, represent an alkyl, aryl, acyloxyalky, or heterocycle group, to form an α-ketophosphonate represented by formula (III), contacting the α-ketophosphonate obtained in the previous step with at least one silyl phosphite represented by formula (IV) as defined hereinabove, hydrolysis of the compounds obtained in the previous step.

More specifically, when $R_1$, $R_2$ and $R_3$ are different from a hydrogen atom, the silyl phosphite represented by formula (IV) which is preferably used corresponds to a compound represented by formula (IV) wherein x is equal to 2.

More specifically, when $R_1$ and $R_2$ are different from a hydrogen atom and $R_3$ is a hydrogen atom, the silyl phosphite represented by formula (IV) which is preferably used corresponds to a compound represented by formula (IV) wherein x is equal to 3.

When $R_1$ is different from a hydrogen atom and $R_2$ is a hydrogen atom, the method for producing compounds represented by formula (I) advantageously comprises the following steps:

contacting at least one acid halide represented by formula (II): ACOX; with at least one silyl phosphite represented by formula (IV):

$$P[(OSialk_3)_x][OR_3]_{3-x} \qquad (IV)$$

wherein $R_3$ is an alkyl, aryl, acyloxyalkyl, or heterocycle group,

A being defined hereinabove,

X represents a halogen atom, preferably chlorine, alk is a C1–6 alkyl group, x is a whole number from 0 to 3, hydrolysis of the compounds obtained in the previous step.

Generally, the contacting step with the silyl compound is advantageously carried out under stoichiometric conditions. However, when one wishes to obtain compounds represented by formula (I) in which $R_1$ and $R_3$ are different from a hydrogen atom and $R_2$ is a hydrogen atom, the method of preparation is advantageously carried out by reacting at least 1 molar equivalent of at least one acid halide represented by formula (II): ACOX, with at least 2 molar equivalents of at least one silyl phosphite represented by formula (IV).

The method of preparation of compounds represented by formula (I) when $R_1$ is different from a hydrogen atom and $R_2$ and $R_3$ represent a hydrogen atom, is advantageously carried out by contacting at least one acid halide represented by formula (II): ACOX, with at least one silyl phosphite represented by formula (IV) wherein x is equal to 2 and contacting the product so obtained with at least one silyl phosphite represented by formula (IV) wherein x is equal to 3.

The hydrolysis in the method of preparation of compounds represented by formula (I) is generally carried out in a solvent capable of donating protons, such as notably methanol or ethanol. Preferably, methanol is the solvent utilized.

The yields of compounds of formula (I) are virtually quantitative. Furthermore, this method has the advantage of implementing the abovementioned steps successively in situ, without the need of transferring products.

Generally speaking, the steps of the method according to the invention may be carried out at room temperature (18–30° C.) and at atmospheric pressure. Of course, those skilled in the art can vary these conditions, where necessary.

More specifically, it should be pointed out that reactions with silyl phosphite may be exothermic, although without occurrence of side reactions. This exothermic nature may make it necessary to carry out these reactions at temperatures below room temperature, more particularly at temperatures between −70° C. and 20° C., especially when using nitrobenzoyl chloride.

The steps preceding the hydrolysis step in the method according to the invention may be carried out in bulk or in a solvent such as $CHCl_3$, THF, $CH_3CN$, $CH_2Cl_2$, or ether. In an advantageous manner, they are carried out in bulk.

The hydrolysis step is advantageously carried out for 1 to 4 hours, more specifically for about 2 hours. It is preferably carried out at room temperature, between 18 and 30° C.

After the hydrolysis step, the method according to the invention preferably comprises purification of the resulting compound represented by formula (1). Such purification is performed by any known means. Preferably, a purification is performed by at least two successive washes in a suitable solvent, particularly ether.

The starting products of the method according to the invention are commercially available products which are therefore easy to obtain. With regard to the phosphites, tris trimethylsilyl phosphite is commercially available. The other phosphites may be prepared as follows. The dialkylphosphite is treated with a concentrated ammonia solution at 0° C. After evaporation of the water, the resulting salt is treated with hexamethyldisilazane for 4 hours under reflux. The reaction is outlined below.

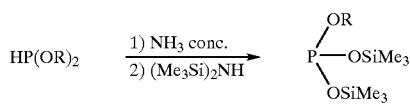

Reaction diagrams of the method according to the invention are depicted in FIG. 1.

According to the present invention, phenylacetic bisphosphonic acid can be prepared similar to the method described in French patent FR 2669348 and by Y. Leroux et al., Phosphorus, Sulfur and Silicon, 63, 181 (1991) for the preparation of hydroxydiphosphonic acid derivatives. According to such method, in a first step, an acid chloride of formula (II) ACOX is caused to react with a mixture of dimethylphosphite and trimethylphosphite, and then in a second step, the ester functions obtained in the previous step are hydrolyzed by acid hydrolysis, followed if necessary by a salification.

The acid chloride used in the first step is phenylacetyl chloride (C6H5-CH2-COCl) and the reaction is preferably carried out in a solvent such as chloroform at a temperature below 30° C., for example at room temperature or at a temperature near 0° C., under neutral atmosphere, for example in a nitrogen atmosphere.

The hydrolysis of ester functions, in the second step, can be carried out by dissolving the product obtained in the first step in concentrated hydrochloric acid, in excess, and refluxing during about 5 to 15 hours.

Phenylacetic bisphosphonic acid prepared as indicated above is obtained with a very high yeld, higher than 95%.

Another object of the present invention relates to any pharmaceutical composition comprising in a pharmaceutically acceptable support at least one compound represented by formula (I) or (I') such as described hereinabove.

In an advantageous manner, this is a pharmaceutical composition intended for the treatment or prophylaxis of disorders characterized by abnormal calcium metabolism, such as cancers or osteoporosis, wherein $R_1$, $R_2$ and $R_3$, which are the same or different, each represent a hydrogen atom, an alkyl, aryl, acyloxyalkyl or heterocycle group, and R' and R", which are the same or different, each represent a hydrogen atom, an alkali metal or alkaline earth atom, A represents a group with the formula —$(CH_2)n$-$R_4$, $R_4$ represents a hydrogen atom, an alkyl group, an aryl group, a heterocycle or a group with the formula —$NR_5R_6$, $R_5$ and $R_6$, which are the same or different, represent a hydrogen atom or an alkyl group, n is a whole number from 0 to 24 inclusive, their optical and geometrical isomers, their racemates, their salts, their hydrates and their mixtures.

The cancers are more specifically breast and prostate cancers and leukemias.

Malignant solid tumors are classified as carcinomas (95%) and sarcomas (5%). Development of carcinomas and sarcomas is correlated with vascularization of the tumor, known as angiogenesis. Any inhibition of this angiogenesis in the tumor makes it possible to shrink, or at least stop or delay tumor growth. Now, it has been found in a surprising manner that compounds of the invention not only have an effect on tumors, but also an effect on angiogenesis.

The pharmaceutical composition according to the invention may be useful notably for the treatment of malignant tumors, more specifically for the treatment of malignant solid tumors.

They may also be used to partially or totally inhibit tumor angiogenesis.

The pharmaceutical composition according to the invention may also be useful for the treatment of viral or inflammatory hepatic diseases. Regarding this particular aspect, the pharmaceutical composition comprises advantageously compounds of formula (I') or phenylacetic bisphosphonicacid or salts thereof.

The invention is also directed to the method of treatment or prophylaxis in the human or animal body by administering to a subject, in particular a mammal and more specifically a human being, in need of such treatment at least one compound of formula (I) or (I') such as defined hereinabove.

It further relates to a method of treating a disorder characterized by abnormal calcium metabolism, such as cancers or osteoporosis, comprising administering to a subject, in particular a patient, in need of such treatment a therapeutically effective amount of at least one compound represented by formula (I) or (I') as defined above, wherein $R_1$, $R_2$ and $R_3$, which are the same or different, each represent a hydrogen atom, an alkyl, aryl, acyloxyalkyl or heterocycle group, and R' and R", which are the same or different, each represent a hydrogen atom, an alkali metal or alkaline earth atom, A represents a group with the formula —$(CH_2)n$-$R_4$, $R_4$ represents a hydrogen atom, an alkyl group, an aryl group, a heterocycle or a group with the formula —$NR_5R_6$, $R_5$ and $R_6$, which are the same or different, represent a hydrogen atom or an alkyl group, n is a whole number from 0 to 24 inclusive, their optical and geometrical isomers, their racemates, their salts, their hydrates and their mixtures.

Another object of the present invention is a method for treating viral or inflammatory hepatic disease, comprising administering to a patient in need of such treatment a therapeutically effective amount of at least one compound represented by formula (I) or (I') as defined above, wherein $R_1$, $R_2$ and $R_3$, which are the same or different, each represent a hydrogen atom, an alkyl, aryl, acyloxyalkyl or heterocycle group, and R' and R", which are the same or different, each represent a hydrogen atom, an alkali metal or alkaline earth atom, A represents a group with the formula —$(CH_2)$n-$R_4$, $R_4$ represents a hydrogen atom, an alkyl group, an aryl group, a heterocycle or a group with the formula —$NR_5R_6$, $R_5$ and $R_6$, which are the same or different, represent a hydrogen atom or an alkyl group, n is a whole number from 0 to 24 inclusive, their optical and geometrical isomers, their racemates, their salts, their hydrates and their mixtures.

With respect to these methods of therapeutic treatment and compositions useful for these methods, and in a particular aspect, the compounds are of formula (I) or (I'), with the exception of compounds of formula (I) wherein $R_1$, $R_2$ and $R_3$ simultaneously represent a hydrogen atom, and compounds represented by formula (I') in which R' and R" simultaneously represent a hydrogen atom.

Compounds according to the invention exhibit a specific activity, with no side effect and no toxicity, even in the case of a long lasting treatment. Pharmacological and clinical studies have demonstrated that compounds of the present invention, for instance phenyl acetic bisphosphonic acid, has anti-tumor, anti-angiogenic and pro-apoptotic affects, and that they are active both in vivo and in vitro against the proliferation of numerous tumor cell lines. For example, in vitro, phenylacetic bisphosphonic acid inhibits the proliferation of two breast cancer cell lines, representatives of two types of breast cancers (non metastasic hormonosensitive tumor and metastasic hormonoindependent tumor) even at a low dose, by breaking the cellular cycle and by inducing an apoptosis of tumor cells. In vivo, phenylacetic bisphosphonic acid irreversibly blocks the proliferation of MCF7-ras cells and the growth of mammary tumors in the first five or six weeks of treatment, and this effect is maintained without any toxic affect, even when the treatment is applied during a long period of time. The in vivo and in vitro results thus demonstrate the proapoptotic and antiangiogenic effect of the compounds according to the invention. Such assays are detailed in the examples thereafter.

Further, studies have demonstrated the action of phenylacetic bisphosphonic acid on hepatic inflammatory lesions induced by viruses.

These results show that phenylacetic bisphophonic acid and the pharmaceutically acceptable salts, partially esterified, or derivatives thereof can be efficiently used in the treatment of cancers and more particularly human breast or prostate cancer, and also in the treatment of inflammatory hepatic diseases, such as acute and chronic hepatitis, for example viral or toxic hepatitis.

The antiangiogenic activity is also of interest in the treatment of pathologic angiogenesis, for example diabetes retinopathies, rheumatoid polyarthritis and macular degeneration related to age.

The pharmaceutical compositions according to the invention advantageously comprise one or more pharmaceutically acceptable excipients or vehicles. Some examples include saline, physiological, isotonic, buffered solutions, etc., compatible with pharmaceutical use and known to those skilled in the art. The compositions may contain one or more agents or vehicles chosen among dispersives, solubilizers, stabilizers, preservatives, etc. The agents or vehicles that may be used in the formulations (liquids and/or injectables and/or solids) comprise notably methylcellulose, hydroxymethylcellulose, carboxymethylcellulose, polysorbate 80, mannitol, gelatin, lactose, vegetable oils, acacia, etc. The compositions may be formulated as suspensions for injection, gels, oils, tablets, suppositories, powders, capsules, gelules, etc., possibly by means of pharmaceutical forms or devices allowing sustained and/or delayed release. For this type of formulation, an agent such as cellulose, carbonates or starches is advantageously used.

The compounds or compositions according to the invention may be administered in various ways and in different forms. For instance, they may be injected by the systemic route or given orally, preferably by the systemic route, such as, for example, by the intravenous, intramuscular, subcutaneous, transdermal, intra-arterial route, etc. For injections, the compounds are generally packaged as liquid suspensions, which may be injected by means of syringes or infusions, for example. It is understood that the rate and/or dose injected may be adapted by those skilled in the art according to the patient, the pathology, the method of administration, etc. Typically, the compounds are administered at doses ranging from 0.1 µg to 500 mg/kg of body weight, more generally from 0.01 to 10 mg/kg, typically between 0.1 and 10 mg/kg. Furthermore, repeated injections may be given as the case may be. Moreover, the compositions according to the invention may additionally comprise other active substances or agents.

Other aspects and advantages of the present invention will become apparent from the following examples, which are given for purposes of illustration and not by way of limitation.

EXAMPLES

Unless otherwise indicated, percentages are expressed by weight. Y: yield.

Preparation of Compounds According to the Invention

Preparation of 1-hydroxy-1-phenylethylidene-1,1-bisphosphonic acid

To a mixture of trimethylphosphite (0.01 mole) and dimethylphosphite (0.01 mole) in 5 ml of chloroform, was added dropwise a solution phenylacetyl chloride in 5 ml of chloroform at 0° C., while stirring the reaction mixture under dry nitrogen. The mixture is then heated to 80° C. for about 8 hours.

After cooling, the mixture is washed and precipitated in ethyl ether. The white solid collected by filtration is the bisphosphonate ester (1-hydroxy-1-phenylethylidene-1,1-bisphosphonate tetramethyl ester).

Yield: 97%

Melting point F=120° C.

NMR $P^{31}$ ($CDCl_3$): δ=20.53 ppm

NMR $H^1$ (TMS, $CDCl_3$): δ=3.8 ppm; $δ_{t(CH2)}$=3.4 ppm ($^3J_{HCCP}$: 13.5 Hz); $δ_{m(ph)}$=7.3 ppm.

The bisphosphonate ester obtained as indicated above is redissolved in a large excess of concentrated hydrochloric aqueous acid and then refluxed for 15 hours. The aqueous solution is washed with ether, and then evaporated under vacuum on Rotavapor. The corresponding acid is thus obtained.

The acid is purified and reprecipitated in ether and in a benzene/ether mixture. The white precipitate is collected by filtration to produce 1-hydroxy-1-phenylethylidene-1,1-bisphosphonic acid.

Yield: 98%
NMR $P^{31}$ ($D_2O$): δ=19.53 ppm
NMR $H^1$ ($D_2O$): $δ_{t(CH2)}$=3.4 ppm ($^3J_{HCCP}$: 13.5 Hz); $δ_{m(ph)}$=3.4 ppm.

Preparation of methyl-di(trimethylsilyl)phosphite

In a four-necked flask equipped with a mechanical stirrer, coolant, introduction ampoule, thermometer and nitrogen inlet valve are added dropwise 100 ml of concentrated ammonia solution in 83 g of dimethylphosphonate previously distilled if necessary. The solution obtained is evaporated under reduced pressure. After repeated co-evaporations with pyridine (100 ml) and benzene (2×100 ml), the white solid obtained is treated with 140 ml of hexamethyldisilazane. The resulting mixture is refluxed for 6 hours. The solution is then distilled to yield the expected compound.

Yield=58% BP 74–76 (20 mm Hg)
$^{31}P$ {1H} NMR ($CDCl_3$): δ=127.6 $^1H$ NMR ($CDCl_3$): δ=0.19 (s, 18H, $Me_3Si$), 3.30 (d, 3H, $J_{PH}$=8 Hz, MeO).

Method of Synthesis of 1-hydroxymethylene-1,1-bisphosphonic acid.

One equivalent of acid chloride is placed in a three-necked flask equipped with a magnet under an inert atmosphere (Ar). Two equivalents of tris(trimethylsilyl)phosphite are added at room temperature with stirring. The solution is then left to stand for several minutes at room temperature. The hydrolysis is carried out in methanol at 25° C. for 1 hour. Volatile fractions are evaporated under vacuum. The products are purified by an ether wash.

(1-hydroxy-1-phosphono-ethyl)-phosphonic acid. White powder. Yield=98%.

$^{31}P$ {1H} NMR ($D_2O$): δ=19.4 $^1H$ NMR ($D_2O$): δ=1.48 (t, 3H, $^3J$=16 Hz, $CH_2COH$).

(1-hydroxy-1-phenyl-phosphono-ethyl)-phosphonic acid. White powder. Yield=90%.

$^{31}P$ {1H} NMR ($D_2O$): δ=19.0. $^1H$ NMR ($D_2O$): δ=3.31 (t, 2H, $^3J$=14 Hz, $CH_2COH$), 7.26–7.32 (m, 4H, $C_6H_5$), 7.38 (t, 1H, $^3J$=7.5 Hz, $C_6H_5$).

(Hydroxy-phenyl-phosphono-methyl)-phosphonic acid. White powder. Yield=91%.

$^{31}P$ {1H} NMR ($D_2O$): δ=16.0. $^1H$ NMR ($D_2O$): δ=7.08–7.13 (m, 4H, $C_6H_5$), 7.46 (t, $^3J$=5 Hz, 1H, $C_6H_5$). $^{13}C$ {1H} NMR ($D_2O$): δ=78.76 (t, $^1J$=145.75 Hz, COH), 128.9, 130.8, 131.2, 138.6 ($C_6H_5$).

(Hydroxy-p-nitrophenyl-phosphono-methyl)-phosphonic acid. White powder. Yield=85%.

$^{31}P$ {1H} NMR ($D_2O$): δ=15.3. $^1H$ NMR ($D_2O$): δ=7.89 (d, 2H, $^3J$=8.5 Hz, $C_6H_4$), 8.15(d, 2H, $^3J$=8.5 Hz, $C_6H_4$). $^{13}C$ {1H} NMR ($D_2O$): δ=75.28 (t, $^1J$=149 Hz, COH), 124.67, 128.15; 146.13, 148.35 ($C_6H_4$).

General Operating Procedure for Products of the Type A—C(OH)PO(OH)$_2$PO(OMe)$_2$ In a four-necked flask equipped with a mechanical stirrer, coolant, introduction ampoule, thermometer and nitrogen inlet valve are added dropwise 1 equivalent of trimethylphosphite in 1 equivalent of acid chloride at 0° C. After a 2 hour reaction time at room temperature, the dimethyl α-ketophosphonate is completely formed (the reaction is followed by $^{31}P$ NMR). One equivalent of tris(trimethylsilyl)phosphite is then added dropwise. The solution is then stirred for 15 minutes. Methanol is then added and the solution stirred for 2 hours at room temperature. The solvent and volatile fractions are then evaporated. The resulting product is a white powder which is purified by successive washes with ether.

[(Dimethoxy-phosphoryl)-hydroxy-phenyl-methyl]-phosphonic acid

White powder. Yield=91%
$^{31}P$ {1H} NMR ($D_2O$): δ=23.58 (d, $^2J$=27 Hz); 12.92 (d, $^2J$=27 Hz). $^1H$ NMR ($D_2O$): δ=7.73 (d, 2H, $^3J$=6.0 Hz, $C_6H_5$); 7.46–7.43(m, 3H, $C_6H_5$); 3.79(d, 3H, $^3J$=10.0 Hz, $OCH_3$); 3.63 (d, 3H, $^3J$=10.0 Hz, $OCH_3$).

[(Dimethoxy-phosphoryl)-hydroxy-ethyl]-phosphonic acid

White powder. Yield=91%
$^{31}P$ {1H} NMR ($D_2O$): δ=29.1 (d, $^2J$=27 Hz); 19.90 (d, $^2J$=27 Hz). $^1H$ NMR ($D_2O$): δ=7.73 (d, 2H, $^3J$=6.0 Hz, $C_6H_5$); 7.46–7.43(m, 3H, $C_6H_5$); 3.79(d, 3H, $^3J$=10.0 Hz, $OCH_3$); 3.63 (d, 3H, $^3J$=10.0 Hz, $OCH_3$).

General Operating Procedure for Products of the Type A-C(OH)PO(OH)OMePO(OH)(OMe)

In a four-necked flask equipped with a mechanical stirrer, coolant, introduction ampoule, thermometer and nitrogen inlet valve are added dropwise 2 equivalents of methyl-bis(trimethylsilyl)phosphite in 1 equivalent of chloride. After a 10 minute reaction time at room temperature, the solution is methanolysed for 2 hours. The solvent and volatile fractions are then evaporated. The resulting product is a white powder which is then purified by successive washes with ether.

Monomethyl ester of [hydroxy-(hydroxy-methoxy-phosphoryl)-phenyl-methyl]phosphonic acid.

White powder. Yield=90%
$^{31}P$ {1H} NMR ($D_2O$): δ=18.50. $^1H$ NMR ($D_2O$): δ=7.43–7.41 (m, 2H, $C_6H_5$); 7.15–7.05 (m, 3H, $C_6H_5$); 3.79(d, 6H, $^3J$=6.0 Hz, $OCH_3$)

Monomethyl ester of [(hydroxy-(hydroxy-methoxy-phosphoryl)-ethyl]phosphonic acid White powder. Yield=90%
$^{31}P$ {1H} NMR ($D_2O$): δ=23.9. $^1H$ NMR ($D_2O$): 2.96(d, 6H, $^3J$=6.0 Hz, $OCH_3$); 1.07–0.98 (m, 3H, $CH_3$).

Monomethyl ester of [gydroxy-(hydroxy-methoxy-phosphoryl)-2-phenyl-ethyl]phosphonic acid.

White powder. Yield=90%
$^{31}P$ {1H} NMR ($D_2O$): δ=20.79. $^1H$ NMR ($D_2O$): δ=7.26–7.11 (m, 5H, $C_6H_5$); 3.79(d, 6H, $^3J$=6.0 Hz, $OCH_3$); 3.15 (t, 2H, $^3J$=10.0 Hz, $C_6H_5$—$CH_2$)

General Operating Procedure for Products of the Type A-C(OH)PO(OH)(OMe)PO(OMe)$_2$ In a four-necked flask equipped with a mechanical stirrer, coolant, introduction ampoule, thermometer and nitrogen inlet valve are added dropwise 1 equivalent of trimethylphosphite in 1 equivalent of acid chloride at 0° C. After a 2 hour reaction time at room temperature, the dimethyl α-ketophosphonate is completely formed (the reaction is followed by $^{31}P$ NMR). One equivalent of methyl bis(trimethylsilyl)phosphite is then added dropwise. The solution is then stirred for 15 minutes. Methanol is then added and the solution is stirred for 2 hours at room temperature. The solvent and volatile fractions are then evaporated. The resulting product is a colorless oil. It is purified by successive washes with ether.

Dimethyl ester of [hydroxy-(hydroxy-methoxy-phosphoryl)-phenyl-methyl]-phosphonic acid White powder. Yield=90%.

$^{31}P$ {1H} NMR (CDCl$_3$): δ=16.74 (d, $^2J$=47 Hz); 14.52 (d, $^2J$=47 Hz). $^1H$ NMR (D$_2$O): δ=8.60–8.40 (s, 2H, OH); 7.49 (d, 2H, $^3J$=8.0 Hz, C$_6$H$_5$); 7.04–6.97(m, 3H, C$_6$H$_5$); 3.47(d, 3H, $^3J$=10.0 Hz, OCH$_3$); 3.34 (d, 3H, $^3J$=10.0 Hz, OCH$_3$); 3.23 (d, 3H, $^3J$=10.0 Hz, OCH$_3$).

Dimethyl ester of [hydroxy-(hydroxy-methoxy-phosphoryl)-ethyl]-phosphonic acid $^{31}P$ {1H} NMR (CDCl$_3$): δ=20.46 (d, $^2J$=48 Hz); 18.67 (d, $^2J$=48 Hz). $^1H$ NMR (D$_2$O): δ=8.98 (s, 2H, OH) 3.92(d, 3H, $^3J$=10.0 Hz, OCH$_3$); 3.88 (d, 3H, $^3J$=10.0 Hz, OCH$_3$); 3.86 (d, 3H, $^3J$=10.0 Hz, OCH$_3$); 1.67 (t, 3H, $^3J_{H-P}$=15.5 Hz).

Anti-Proliferative and Anti-Invasive Activities of the Compounds According to the Invention Two bisphosphonates designated as BP1 and BP2 whose formulas are shown below were tested in cell and animal models. BP1 was not partially esterified and serves as a comparative example.

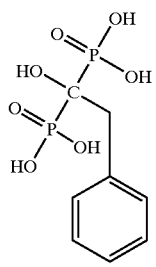

BP1

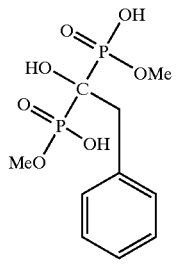

BP2

In vitro Tests

Materials and Methods:

The bisphosphonates BP1 and BP2 were tested in different cell lines:

FRCjun MRA, a murine fibrosarcoma cell line produced by transfection of FR3T3 cells by the oncogene jun-4, A 431 human carcinoma cells. These cells harbor a VEGF (vascular endothelial growth factor) autocrine loop and, after implantation in immunosuppressed mice, induce rapid development of highly angiogenic tumors.

MDA MB 435 human breast tumor cells,

HUV-EC-C, transformed human umbilical cord endothelial cells (HUVEC),

BBC, bovine cerebral capillary endothelial cells.

Cell proliferation in the presence of different concentrations of BP1 or BP2 was measured by an MTT test after 24, 48 and 72 h of culture.

In vitro Test Results:

The bisphosphonates (0.1–2 mM) inhibit the proliferation of FRCjunMRA, MDA MB 435 and A 431 cells in a time- and dose-dependent manner (FIGS. 2 and 3). For example, BP2 (2 mM) inhibits the proliferation of the three cell lines by 40%, 60% and 30%, respectively, after 48 h of culture. After 72 h in the presence of BP2 (2 mM), proliferation of A 431 cells is inhibited by 80% (P<0.05) (FIG. 3).

A trypan blue exclusion test shows that BP1 and BP2 do not induce cytotoxicity, even at concentrations above 5 mM.

Furthermore, the bisphosphonates (0.1–2 mM) also inhibit the proliferation of HUV ECC and BBC endothelial cells in a time- and dose-dependent manner.

Toxicity Tests

Tumor-free immunosuppressed mice were treated with BP1 and BP2 at doses ranging from 0.06 to 6 mg per injection and per animal. Mice received one injection per day for one week. Animals were weighed before, during and after treatment.

BP1 doses less than 6 mg/injection and all BP2 doses tested (0.06–6 mg/injection) caused no signs of toxicity such as hair loss, diarrhea, infection or anemia in the treated animals.

In vivo Tests

Materials and Methods:

A 431 cells were injected subcutaneously into immunosuppressed mice. The mice developed tumors within one week. Tumor-bearing mice were assigned randomly to a control group or to treatment groups receiving different concentrations of BP1 and BP2.

Mice received twice weekly by subcutaneous injection near the tumor either 0.1 ml of PBS alone for the controls (n=6), or PBS containing either BP1 or BP2 at the following doses: 0.006 (n=6); 0.06 (n=6) or 0.6 mg/injection (n=6). Tumors were measured weekly and their volume V calculated by the formula:

$V=(4/3)\pi R1^2 R2$ wherein $R1$ is radius 1 and $R2$ radius 2, with $R1 < R2$.

Animals were sacrificed and the tumors excised, then weighed, fixed, embedded in paraffin and sliced. Endothelial cells from tumor blood vessels laid down during tumor angiogenesis were visualized by immunohistochemical methods (GSL 1). Tumor angiogenesis was evaluated by image analysis with NIH image software.

In vivo Test Results

Treatment with bisphosphonates inhibited the growth of A 431 tumors and was maximal even at the lowest doses (FIG. 4). After 5 weeks of treatment, BP1 and BP2 (0.6 mg/injection/mouse) inhibited the growth of A 431 tumors by 40% and 56%, respectively (P<0.05).

In contrast to the in vitro results, the in vivo results show that BP2 has greater efficacy than BP1.

Furthermore, inhibition of the growth of A 431 tumors in the treated animals was correlated with inhibition of intratumoral angiogenesis (FIG. 5). Such inhibition, demonstrated by a significant decrease in endothelial cell area per unit of area, was observed starting from the lowest doses of BP1 and BP2.

To our knowledge, the synthesized bisphosphonates are the first to show antitumoral action in vivo on the primary tumor, their effects being correlated with an inhibition of angiogenesis.

In vitro Study of Sodium Phenylacetate Bisphosphonate

The study of the effect of sodium phenylacetate bisphosphonate on cell growth and cell viability has been carried out as indicated hereafter.

MCF7-ras cells are cultivated (20,000 cells/well), on a dish of 24 wells. After incubation for 24 hours, the medium (DMEM with 10% foetal calf serum) is replaced with the same medium to which are added various concentrations of phenylacetate bisphosphonate (2 mM, 4 mM, 6 mM, 8 mM and 10 mM). The cells are incubated for 1 to 4 days at 37° C. The cell viability is controlled by the Trypan blue test.

It is then noticed that phenylacetate bisphosphonate is cytostatic for the three first days of culture when concentrations are lower than 6 mM. For higher concentrations (8 et 10 mM) a slight toxicity (10%) is observed, which becomes more important (50–60%) by the fourth day of culture.

In order to check the reversibility of the effect of phenylacetate bisphosphonate, MCF7-ras cells have been treated with increasing concentrations of phenylacetate bisphosphonate for 10 days, the medium being changed every two days. The cells are divided in two groups. The DMEM medium supplemented with 10% of foetal calf serum is added to the first group, and the same medium with 10 mM of phenylacetate bisphosphonate is added to the second group, the medium being changed every two days. After 15 days, tritiated thymidine is added during 4 hours and the radioactivity of the suspension is determined by using a beta liquid scintigraphic counter (Beckman).

An inhibition of the cells proliferation is observed which is partially reversible at the dose of 2 mM, and which is irreversible at a dose above 4 mM.

Proapoptotic Activity of Sodium Phenylacetate Bisphosphonate

In order to determine the nature of the toxicity of sodium phenylacetate bisphosphonate, MCF7 and MCF7-ras cells are cultivated, and then washed after 24 hours, and cultivated for 3 hours in DMEM medium with 10% of foetal calf serum. Phenylacetate bisphosphonate (10 mM) is added to one group but not to the other group. Apoptosis is determined by the test of Annexine V conjugated with FITC antibody. Propidium iodide is used in order to determine early apoptosis (positive staining for Annexine V and negative staining with propidium iodide) and late apoptosis (positive staining with Annexine V and with propidium iodide).

After 4 hours of treatment with phenylacetate bisphosphonate, the percentage of cells in early apoptosis is almost identical in the two cell types, whilst the percentage of cells in late apoptosis is more important with MCF7-ras cells (22% and 53% respectively).

The cell apoptosis is confirmed by the method of DNA degradation. MCF7 and MCF7-ras cells are cultivated ($5 \times 10^5$ cells in T25 flasks). After 24 hours, the cells are washed, and then cultivated in DMEM medium with 10% of foetal calf serum; phenylacetate bisphosphonate (10 mM) is added to one group, and no phenylacetate bisphosphonate is added to the other group.

After 96 hours, the cell extract containing the fragmented DNA is incubated with 0.5 mg/ml of RNase A at 37° C. for one hour, then with 0.5 mg/ml of proteinase K for one hour at 37° C. After incubation, the fragmented DNA is precipitated by isopropanol and then dissolved in 10 mM of Tris-HCl (pH 8) 1 ml pf EDTA, 5% of glycerol and 0.05% bromophenol blue. The fragmented DNA separated by electrophoresis on agarose gel at 1% is marked with ethidium bromide and photographed in UV.

A dramatic degradation of DNA of MCF7 and MCF7-ras cells is then observed in the group containing 10 mM of phenylacetate bisphosphonate.

Theses results demonstrate that phenylacetic bisphosphonic acid inhibits the proliferation and induce the apoptosis MCF7 and MCF7-ras cells.

In vivo Study of Sodium Phenylacetate Bisphosphonate

The antitumor effect of sodium phenylacetate bisphosphonate is verified in mice.

Inoculation of $4 \times 10^6$ MCF7-ras cells in female athymic nude mice is made sub-cutaneously in a 0.1 ml volume of DMEM, which induces 70% of tumors after three weeks.

Treatment with phenylacetate bisphosphonate begun when the mean volume of the tumors was 550 mm$^3$. The animals are divided in two groups, on receiving phenylacetate bisphosphonate, and the other no. Phenylacetate bisphosphonate is injected sub-cutaneously and peritumorally, twice a week, during 5 weeks, and the doses are 80 mg/kg (5 cases) and 160 mg/kg (6 cases).

At the end of the treatment, an inhibition of the growth of the tumors is observed; it is irreversible and dose dependent. When the treatment is stopped, the growth of the tumors is blocked for at least three weeks in the case of the mice treated with a 160 mg/kg dose, whilst tumor growth relapsed is observed in the case of mice treated with a 80 mg/kg dose.

The immunohistologic analysis of the tumors show that the decrease in tumor growth is related to induction of apoptosis, to a sharp decrease of angiogenesis of the tumor and induction of fibrose in the tumor.

Pro-apoptotic Effet

Further, the proapoptotic effect of phenylacetate bisphosphonate is confirmed by the technique of antibody staining. The staining of apoptotic cells is made by the M30 antibody which recognises the specific site of caspases on the cytokeratine 18 filaments produced by the epithelial cells. Such filaments rapidly aggregate in the cells in early apoptosis, by hyperphosphorylation of cytokeratines. By this cytoplasmic staining, granular structures are observed inside the cytoplasm, which corresponds to cells in late apoptosis.

These granular structures are observed in the tumor which have been treated with a high dose (160 mg/kg) of phenylacetate bisphosphonate. Further, an increase in the staining with anticytokeratine 18 antibody with concentration dose-dependently is noticed. By this way, early apoptosis is clearly distinguished from late apoptosis by the presence of granular structures in the cytoplasm.

This confirms that the treatment of tumors with phenylacetate bisphosphonate with a 80 mg/kg dose results in a apoptosis whilst the treatment with a 160 mg/kg dose results in a aponecrosis, which is an intermediate state between apoptosis and necrosis.

Anti-angiogenic Effect

The anti-angiogenic was verified by the GSL1 lectin method.

By using GSL1 lectin, angiogenesis is determined and identified by the red coloration staining of endothelial cells with anti-GSL1 antibody. It is noted that this angiogenesis is inhibited by the treatment of the tumors with phenylacetate bisphosphonate. This effect is partial but important (80%) at the 80 mg/kg dose. and complete at 160 mg/kg.

These assays demonstrate that phenylacetic bisphosphonic acid exhibits a very important antiangiogenic effect, and also a antitumor and proapoptotic effect. These results confirm that phenylacetic bisphosphonic acid is a potentially active medicament for the treatment of cancer tumors, more particularly breast cancer.

Effect on Inflammatory Hepatic Cells

The study is carried out on nude mice having an acute hepatitis. The mice are divided in two groups, one being treated with sodium phenylacetate bisphosphonate, whilst the second is not. Phenylacetate bisphosphonate is administered to the treated mice sub-cutaneously (80 mg/kg or 160 mg/kg), twice a week for five weeks. The mice are sacrificed and the liver is histologically analyzed after HES (method of Hematoxiline Eosine Staining).

Examination with optical microscope shows that the livers of the non-treated mice is seriously damaged by comparison with the treated mice. More particularly, necrotic areas resulting from chronic hepatitis are noted, and also liquids accumulation in the hepatocytes (steatose) associated with a lymphocyte cells inflammation. Such hepatic condition results in the hepatic tissues necrosis, and the formation of the fibrous area.

In contrast, in the case of the mice treated with phenylacetate bisphosphonate, in 4 cases out of 5, hepatic toxicity has been noted.

GENERAL BIBLIOGRAPHY ON THE SUBJECT

Adami S. and Zamberlan N. (1996). Adverse effects of bisphosphonates. A comparative review. Drug Saf., 14, 158–170.

Boissier S., Ferrerras M., Peyruchaud O., Magnetto S., Ebetino F., Colombel, Delmas P., Delaissé J M and Clézardin P. (2000). Bisphosphonates inhibit breast and cancer prostate carcinoma cell invasion, an early event in the formation of bone metastases. Cancer Res., 60, 2949–2954.

Boissier S., Magnetto S., Frappart L., Cuzin B., Ebetino F., Delmas P. and Clézardin P. (1997). Bisphosphonates inhibit prostate and breast carcinoma cell adhesion to unmineralized and mineralized bone extracellular matrices. Cancer Res., 57, 3890–3894.

Diel I., Solomayer E. and Bastert G. (2000). Bisphosphonates and the prevention of metastasis: first evidences from preclinical and clinical studies. Cancer, 88, 3080–3088.

Ezra A., Hoffman A., Breuer E., Alferiev I. S., Monkkonen J., El Hanany-Rozen N., Weiss G., Stepensky D., Gati I., Cohen H., Tormalehto S., Amidon G. L., Golomb G. (2000). A peptide prodrug approach for improving bisphosphonate oralabsorption. J Med Chem., 43, 3641–3652.

Fromigue O., Lagneaux L. and Body J. (2000). Bisphosphonates induce breast cancer cell death in vitro. J. Bone Miner. Res., 15, 2211–2221. Paracrine and autocrine effect of vascular endothelial growth factor: Inhibition of A431 tumor growth and angiogenesis by Carboxymethyl Benzylamide Dextran. Submitted to Cell Growth and Diff.

Hiraga T., Williams P., Mundy G. and Yoneda T. (2001). The bisphosphonate ibandronate promotes apoptosis in MDA MB 231 human breast cancer cells in bone metastases. Cancer Res., 61, 4418–4424.

Ichinose Y., Migita K., Nakashima A., Kawakami A., Aoyagi T. and Eguchi K. (2000). Effects of bisphosphonate on the release of MMP-2 from cultured human osteoblasts. Tohoku J. Exp. Med., 192, 111–118.

Jagdev S., Coleman R., Shipman C., Rostami H. and Croucher P. (2001). The bisphophonate, zoledronic acid, induces apoptosis of breast cancer cells: evidence for synergy with paclitaxel. Br. J. Cancer, 84, 1126–1134.

Lee M., Fong E., Singer R. and Guenette R. (2001). Bisphosphonate treatment inhibits the growth of prostate cancer cells. Cancer Res., 61, 2602–2608.

Lin J. H. (1996). Bisphosphonates: a review of their pharmacokinetic properties. Bone,. 18, 75–85.

Lipton A. (2000) Bisphosphonates and breast carcinoma: present and future. Cancer, 88, 3033–3037.

Luckman S. P., Hugues D., Coxon F., Graham R., Russell G. and Rogers M. (1998). Nitrogen-containing phosphonates inhibit the mevalonate pathway and prevent post-translational prenylation of GTP-binding proteins, including Ras. J. Bone Miner. Res., 13, 581–589.

Mincey B., Moraghan T. and Perez E. (2000). Prevention and treatment of osteoporosis in women with breast cancer. Mayo Clin. Proc., 75, 821–829.

Mondelo N., Peluffo V., Parma., Cointry G., Capozza R., Ferretti J., Piccini E. and Montuori E. (1997). Preclinical toxicology of bisphosphonates. Medicina (B. Aires), 57, 93–100.

Ogihara T., Kikuchi Y., Imai Y., Ohsaka A., Isaka M. and Oka Y. (1995). Acute lymphoblastic leukemia accompagnied by severe hypercalcemia; successful treatment with bisphosphonate. Rinsho Ketsueki, 36, 29–34.

Pade V. and Stavchansky S. (1997). Estimation of the relative contribution of the transcellular and paracellular pathway to the transport of passively absorbed drugs in the Caco-2 cell culture model. Pharm. Res., 9, 1210–1215.

Patashnik S., Rabinovich L. and Golomb G. (1997). Preparation and evaluation of chitosan microspheres containing bisphosphonates. J. Drug Target., 4, 371–380.

Perez-Atayde A., Sallan S., Tedrow U., Connors S., Allred E. and Folkman J. (1997). Spectrum of tumor angiogenesis in the bone marrow of children with acute lymphoblastic leukemia. Am. J. Pathol., 150, 815–821.

Ruifrok P. and Mol W. (1983). Paracellular transport of inorganic and organic ions across the rat ileum. Biochem. Pharmacol., 32, 637–640.

Senaratne S. G., Pirianov G., Mansi J. L., Arnett T. R. and Colston K. W. (2000). Bisphosphonates induce apoptosis in human breast cancer cell lines. Br. J. Cancer, 82, 1459–1468.

Shipman C., Croucher P., Russell R., Helfrich M. and Rogers M. (1998). The bisphosphonate incadronate (YM 175) causes apoptosis of human myeloma cells in vitro by inhibiting the mevalonate pathway. Cancer Res., 58, 5294–5297.

Shipman C., Rogers M., Apperley J., Russell R. and Croucher P. (1997). Bisphosphonates induce apoptosis in human myeloma cell lines: a novel anti-tumor activity. Br. J. Haematol., 98, 665–672.

Shipman C., Vanderkerken K., Rogers M., Lippitt J., Asosingh K., Hughes D., Van Camp B., Russel G. and Croucher P. (2000a). The potent bisphosphonate ibandronate does not induce myeloma cell apoptosis in a murine model of established multiple myeloma. Br. J. Haematol., 111, 283–286.

Takagi M., Takahiashi K., Maruyama T., Kaneko K., Obinata K., Tadokoro R., Kastumata Miura Y., Fujita H., Ishimoto K. and Yabuta K. (1998). Acute lymphoblastic leukemia accompagnied by severe, hypercalcemia: successful treatment including aminohydroxypropylidene bisphosphonate (pamidronate disodium). Pediatr. Hematol. Oncol., 15, 283–286.

Teronen O., Konttinen Y., Lindqvist C., Salo T., Ingman T., Lauhio A., Ding Y., Santavirta S., Valleala H. and Sorsa T.

(1997). Inhibition of matrix metalloproteinase-1 by dichloromethylene bisphosphonate (clodronate). Calcif. Tissue Int., 61, 59–61.

Van der Pluijm G., Vloedgraven H., Van Beek E., Van der Wee-Pals L., Lowik C. and Papapoulos S. (1996). Bisphosphonates inhibit the adhesion of breast cancer cells to bone matrices in vitro. J. Clin. Invest., 98, 698–705.

Van der Pluijm G., Sijmons B., Vloedgraven H., Deckers M., Papapoulos S. and Lowik C. (2001). Monitoring metastatic behavior of human tumor cells in mice with species-specific polymerase chain reaction: elevated expression of angiogenesis and bone resorption stimulators by breast cancer in bone metastases. J. Bone Miner. Res., 16, 1077–1091.

Ylitalo R., Monkkonen J. and Yla-Herttuala S. (1998). Effectes of liposome encapsulated bisphosphonates on acetylated LDL metabolism, lipid accumulation and viability of phagocyting cells. Life Sci., 62, 413–422.

Yoneda T., Michigami T., Yi B., Williams P. J., Niewolna M. and Hiraga T. (2000). Actions of bisphosphonate on bone metastasis in animal models of breast carcinoma. Cancer, 15, 2979–2988.

The invention claimed is:

1. A method of preparation of compounds represented by formula (I):

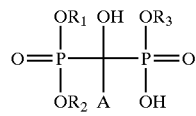

wherein the method comprises the following steps:
(a) contacting a least one acid halide represented by formula (II):

ACOX  (II)

with at least one phosphite represented by formula (V):

P(OR$_1$)(OR$_2$)(OR)  (V)

wherein:
X represents a halogen atom,
A represents a group of formula —(CH$_2$)$_n$—R$_4$,
n is a whole number from 0 to 24 inclusive,
R$_4$ represents a hydrogen atom, an alkyl group, an aryl group, a heterocycle or a group with the formula —NR$_5$R$_6$,
R$_5$ and R$_6$, which are the same or different, represent a hydrogen atom or an alkyl group,
R$_1$, R$_2$ and R, which are the same or different, represent an alkyl, aryl, acyloxyalkyl, or heterocycle group,
to form an α-ketophosphonate represented by formula (III):

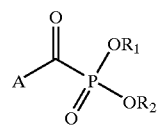

wherein A, R$_1$ and R$_2$ are as defined above;
(b) contacting the α-ketophosphonate obtained in the previous step with at least one silyl phosphite represented by formula (IV):

P[(OSialk$_3$)$_x$][OR$_3$]$_{3-x}$  (IV)

wherein:
alk is a C$_{1-6}$ alkyl group,
x is equal to 2 or 3,
R$_3$ represents a hydrogen atom, an alkyl, aryl, acyloxyalkyl, or heterocycle group; and
(c) hydrolysis of the compounds obtained in the previous step.

2. A method according to claim 1, wherein the silyl phosphite is a compound represented by formula (IV) in which x is equal to 2.

3. A method according to claim 1, wherein the silyl phosphite is a compound represented by formual (IV) in which x is equal to 3.

4. A method of preparation of compounds represented by formula (I):

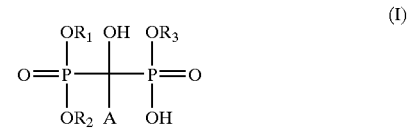

wherein the method comprises the following steps:
(a) contacting at least one acid halide represented by formula (II):

ACOX  (II)

with at least one silyl phosphite represented by formual (IV):

P[(OSialk$_3$)$_x$][OR$_3$]$_{3-x}$  (IV)

wherein:
alk is a C$_{1-6}$ alkyl group,
x is 2,
R$_3$ represents a hydrogen atom, an alkyl, aryl, acyloxyalkyl, or heterocycle group,
X represents a halogen atom,
A represents a group of formula —(CH$_2$)$_n$—R$_4$,
n is a whole number from 0 to 24 inclusive,
R$_4$ represents a hydrogen atom, an alkyl group, an aryl group, a heterocycle or a group with the formula —NR$_5$R$_6$,
R$_5$ and R$_6$, which are the same or different, represent a hydrogen atom or an alkyl group; and
(b) hydroysis of the compounds obtained in the previous step.

5. A method of preparation of compounds represented by formula (I'):

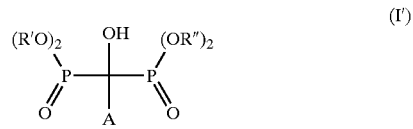

wherein the method comprises the following steps:
(a) an acid chloride of formula (II): ACOX is caused to react with a mixture of dimethylphosphite and trimethylphosphite, wherein
A represents a group of formula —$(CH_2)_n$—$R_4$,
X represents a halogen atom,
n is a whole number from 0 to 24,
$R_4$ represents a hydrogen atom, an alkyl group, an aryl group, a heterocycle or a group with the formula —$NR_5R_6$,
$R_5$ and $R_6$, which are the same or different, represent a hydrogen atom or an alkyl group, and
R' and R", which are the same or different, each represent a hydrogen atom, an alkali metal or alkaline earth atom, with the proviso that both R' and R" are not hydrogen; and (b) then in a second step, the ester functions obtained in the previous steps are hydrolyzed by acid hydrolysis, followed by a salification.

6. A method according to claim 5, wherein the reaction of the first step is carried out in a chlorinated solvent at a temperature below 30° C.

7. A method according to claim 5, wherein the hydrolysis is carried out by dissolving the product obtained in the first step in concentrated hot hydrochloric acid.

8. A method of preparation of compounds represented by formula (I):

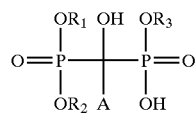
(I)

wherein the method comprises the following steps:
(a) contacting at least one acid halide represented by formula (II):

with at least one silyl phosphite represented by formual (IV)

wherein:
alk is a $C_{1-6}$ alkyl group,
x is 2,
$R_3$ represents a hydrogen atom, an alkyl, aryl, acyloxyalkyl, or heterocycle group,
X represents a halogen atom,
A represents a group of formula —$(CH_2)_n$—$R_4$,
n is a whole number from 0 to 24 inclusive,
$R_4$ represents a hydrogen atom, an alkyl group, an aryl group, a heterocycle or a group with the formula —$NR_5R_6$,
$R_5$ and $R_6$, which are the same or different, represent a hydrogen atom or an alkyl group;

(b) contacting the product obtained in step (a) with at least on silyl phosphite represented by formula (IVa):

wherein:
alk is a $C_{1-6}$ alkyl group,
x is 3,
$R_3$ represents a hydrogen atom, an alkyl, aryl, acyloxyalkyl, or heterocycle group; and
(c) hydroysis of the compounds obtained in step (b).

* * * * *

UNITED STATES PATENT AND TRADEMARK OFFICE
CERTIFICATE OF CORRECTION

PATENT NO. : 7,005,533 B2
APPLICATION NO. : 10/887895
DATED : February 28, 2006
INVENTOR(S) : Marc Lecouvey et al.

It is certified that error appears in the above-identified patent and that said Letters Patent is hereby corrected as shown below:

In column 21, line 35, please delete "contacting a least" and insert in place thereof --contacting at least--.

In column 22, line 14, please delete "formual" and insert in place thereof --formula--.

In column 24, line 6, please delete "formual" and insert in place thereof --formula--.

In column 24, line 24, please delete "on" and insert in place thereof --one--.

In column 24, line 33, please delete "hydroysis" and insert in place thereof --hydrolysis--.

Signed and Sealed this

Twenty-eighth Day of November, 2006

JON W. DUDAS
*Director of the United States Patent and Trademark Office*